United States Patent [19]

Murib et al.

[11] 4,254,039

[45] Mar. 3, 1981

[54] PROCESS FOR THE PREPARATION OF TETRAHYDROFURAN

[75] Inventors: Jawad H. Murib; John M. Inskeep, both of Cincinnati, Ohio

[73] Assignee: National Distillers & Chemical Corp., New York, N.Y.

[21] Appl. No.: 159,980

[22] Filed: Jun. 16, 1980

[51] Int. Cl.³ .......................................... C07D 307/08
[52] U.S. Cl. .............................. 260/346.11; 570/189; 570/234
[58] Field of Search .................................... 260/346.11

[56] References Cited

U.S. PATENT DOCUMENTS 4,002,646  1/1977  Robinson ..................... 260/346.11

Primary Examiner—Richard Raymond
Attorney, Agent, or Firm—Kenneth D. Tremain

[57] ABSTRACT

This invention relates to a process for preparing tetrahydrofuran which comprises reacting a cis-1,4-dihalobutene-2 with water in the presence of a catalytically effective amount of strong acid to provide 2,5-dihydrofuran and thereafter hydrogenating said 2,5-dihydrofuran.

30 Claims, No Drawings

PROCESS FOR THE PREPARATION OF TETRAHYDROFURAN

This application relates to subject matter disclosed in commonly assigned copending U.S. Pat. application Ser. Nos. 159,979, 159,978 and 159,977, each filed of even date herewith.

BACKGROUND OF THE INVENTION

1. Field of the Invention

This invention relates to tetrahydrofuran, and in particular, relates to the manufacture of tetrahydrofuran from cis-1,4-dihalobutene-2.

2. Description of the Prior Art

Tetrahydrofuran is a cyclic ether finding wide and substantial use as a solvent for natural and synthetic resins, especially the vinyl resins, in coatings, adhesives, printing inks, as a chemical intermediate and as a monomer. Tetrahydrofuran has been prepared via the catalytic hydrogenation of furan or 2,5-dihydrofuran, the latter compound being derived from the reaction of acetylene and formaldehyde, and from the dehydrocyclization of 1,4-butanediol or dehydrochlorocyclization of 4-chloro-1-butanol (viz., U.S. Pat. Nos. 2,950,232; 3,156,701; 3,163,660; 3,165,536; 3,467,679; 3,726,905; 4,002,646; 4,093,633; 4,094,887 and, U.K. Pat. Nos. 630,863 and 683,674). Heretofore, attempts to utilize a 1,4-dihalobutene-2 as the starting material required the use of sodium hydroxide followed by hydrogenation to produce a 4-halo-1-butanol or 1,4-butanediol preparative to cyclization to the cyclic ether.

SUMMARY OF THE INVENTION

It has now been surprisingly discovered that if cis-1,4-dihalobutene-2 is reacted with water, i.e., undergoes hydrolysis, in the presence of a catalytically effective amount of a strong acid, 2,5-dihydrofuran is rapidly produced which can thereafter be catalytically hydrogenated in accordance with any of the known procedures to provide tetrahydrofuran.

While not wishing to be bound in any way, it would appear that the aforesaid first stage hydrolysis of cis-1,4-dihalobutene-2 converts the haloalkene to the corresponding olefinic halohydrin or glycol followed by cyclization to 2,5-dihydrofuran. The 2,5-dihydrofuran is then hydrogenated by known methods to produce tetrahydrofuran.

The process of this invention is especially advantageous when employing a mixture of cis and trans-1,4-dihalobutene-2 derived from the halogenation of butadiene. While 3,4-dihalobutene-1 is also a product of the halogenation of butadiene, it is readily isomerized in the presence of an isomerization catalyst, e.g., cuprous chloride, to mixed cis and trans-1,4-dihalobutene-2. Hydrolysis of the mixed cis and trans-1,4-dihalobutene-2 in the presence of a strong acid gives a product mixture of 2,5-dihydrofuran and crotonaldehyde, respectively, and by-product hydrogen haloic acid. The product mixture is easily separated, e.g., by distillation, to provide essentially pure components. The 2,5-dihydrofuran is hydrogenated to provide the desired tetrahydrofuran. The crotonaldehyde is also a valuable component useful in organic synthesis, as a solvent, etc. The hydrogen haloic acid is oxidized and recycled to the halogenation step.

From the above, it will be seen that starting with butadiene, the only additional reactants which are consumed in obtaining tetrahydrofuran and crotonaldehyde are hydrogen and oxygen (advantageously from air). Unlike the process of U.S. Pat. No. 4,093,633 referred to supra, the process of this invention does not require expensive metallic catalysts such as palladium or tellurium. In addition, the process herein utilizes only one mole of halogen compared to two moles of acetic acid for the process of U.S. Pat. No. 4,093,633.

DESCRIPTION OF THE PREFERRED EMBODIMENTS

Among the cis-1,4-dihalobutene-2 starting compounds which can be used herein with good results are included cis-1,4-dichlorobutene-2, cis-1,4-dibromobutene-2, cis-1-chloro-4-bromo-butene-2, cis-1-chloro-4-iodobutene-2, and the like. The cis-1,4-dihalobutenes can be used singly or in admixture. Cis-1,4-dichlorobutene-2 is especially preferred herein due to its relatively low cost and ready availability.

The reaction of the cis-1,4-dihalobutene-2 and water can be carried out with less than the stoichiometrically required amount of water but it is generally preferrable to use a large stoichiometric excess of water, e.g., from about 1.5 to about 10 times the amount calculated.

The hydrolysis reaction herein is catalyzed in the presence of at least one strong acid. The term "strong acid" is intended to be inclusive of all organic and inorganic acids which are highly dissociated in water. Such acids are well known in the art and include hydriodic acid, sulfuric acid, sulfonic acid, especially the arylsulfonic acids, phosphoric acid, phosphonic acid, especially the arylphosphonic acids, and the like. Strong inorganic acids such as hydriodic acid, sulfuric acid and phosphoric acid are particularly advantageous for use as catalysts herein. The amount of strong acid catalyst employed does not seem to be critical and can vary considerably. At least a catalytically effective amount of catalyst should be used, of course. In general, an amount of catalyst which is effective to provide a reasonable reaction rate is sufficient. In practice, an amount of strong acid in the range of from about 0.001 to about 0.1 moles, and preferably from about 0.002 to about 0.025 moles, per mole of cis-1,4-dihalobutene-2, provides good results.

The hydrolysis reaction can be carried out in a solvent which assists the dissolution of the cis-1-4-dihalobutene-2 and which is miscible with water. Such solvents include cyclic ethers such as 2,5-dihydrofuran, tetrahydrofuran, dioxane and tetrahydropyran; ethers such as alkyl ethers of alkylene glycols and polyalkylene glycols; ketones such as acetone; lactones of hydroxy organic acids such as butyrolactone; organic acids such as acetic acid and propionic acid; monoalcohols such as methanol, ethanol and 2-ethylhexanol; glycols such as ethylene glycol and 1,3-propylenediol; and the like. Where it is desirable to use a mutual solvent system for the cis-1,4-dihalobutene-2 and water, it is generally preferred to employ 2,5-dihydrofuran as the solvent for the sake of convenience and simplicity.

Optionally, the process can be carried out in the presence of a phase transfer agent to accelerate the transfer of water to the organic phase of the first stage hydrolysis reaction. In the absence of a phase transfer agent, contact of the cis-1,4-dihalobutene-2 with water proceeds slowly limiting the usefulness of the procedure as a viable commercial synthesis for tetrahydrofuran. Employing a phase transfer agent, the hydrolysis stage herein proceeds at a much faster rate providing an economically efficient route to tetrahydrofuran.

Phase transfer agents useful in the hydrolysis stage include quaternary ammonium or phosphonium salts in which the anion is halide, hydroxide, sulfate, bisulfate, phosphate, and the like, and the alkali metal tetraphenyl boron compounds. Some specific phase transfer agents which can be used herein with good results are tetradecyltrimethylammonium bromide, tetradecyltributylammonium bromide and sodium tetraphenyl boron.

The reaction conditions for the first stage hydrolysis reaction are not overly critical in that wide ranges of temperature and pressures are operable. The practical limitations of production equipment will dictate to a great extent the selection of temperatures and pressure at which the reaction is to be effected. Thus, using available production systems, the selected temperature should be at least about 20° C. and can range up to about 350° C. and even higher. For most purposes, the preferred operating temperature ranges from about 100° to about 250° C. The pressure can range from somewhat below atmospheric to as high as 160 atmospheres. Most desirably, the pressure should be in the range of from about atmospheric to about 50 atmospheres, particularly when employing the aforesaid preferred temperature range. The amount of time required for conversion of the cis-1,4-dihalobutene-2 to 2,5-dihydrofuran will vary according to the specific reaction conditions and in general, is on the order of from about 0.5 to about 12 hours. Optimum yields of 2,5-dihydrofuran for a given set of reaction conditions can be readily determined employing known and conventional techniques as, for example, chromatographic analysis. Hydrogenation of the 2,5-dihydrofuran to tetrahydrofuran can be carried out in situ or, if desired, the 2,5-dihydrofuran can be recovered by any routine technique, e.g., distillation, and thereafter subjected to hydrogenation to provide tetrahydrofuran.

The following examples illustrate the process of the present invention.

EXAMPLE 1

To a 100 ml. Fisher-Porter reactor tube provided with a valve and magnetic stirrer was charged a mixture of:

| | |
|---|---|
| 4.0 ml. | cis-1,4-dichlorobutene-2 |
| 16.0 ml. | deionized water |
| 0.1 ml. | hydriodic acid (57% by weight) |

The tube was sealed and heated in an oil bath maintained at 120° C. for 2 hours. After cooling, the reaction mixture was analyzed by gas chromatography. The analysis indicated that 92.6% of the 1,4-dichlorobutene-2 was converted to a product mixture having a distribution of 80.5% 2.5-dihydrofuran and 19.5% crotonaldehyde.

EXAMPLE 2

Example 1 was repeated except that 0.2 g. of sodium tetraphenyl boron was used as a transfer agent. Gas chromatographic analysis indicated a 1,4-dichlorobutene-2 conversion of 95.6 with a product distribution of 82.5% 2,5-dihydrofuran and 17.5% crotonaldehyde.

EXAMPLE 3

A fraction (10 ml.) of the reaction mixture obtained in Example 2 was subjected to hydrogenation employing 2 g. of 5% palladium on carbon at ambient temperature and a pressure of 50 psi for 3 hours. Analysis showed that the hydrogenation reaction resulted in the conversion of 51% of the 2,5-dihydrofuran to tetrahydrofuran.

EXAMPLE 4

Example 2 was repeated except that trans-1,4-dichlorobutene-2 (90% purity) was used. Gas chromatographic analysis indicated that 60% of the product was crotonaldehyde with trace amounts of 2,5-dihydrofuran.

What is claimed is:

1. A process for preparing tetrahydrofuran which comprises reacting a cis-1,4-dihalobutene-2 with water in the presence of a catalytically effective amount of strong acid to provide 2,5-dihydrofuran and thereafter hydrogenating said 2,5-dihydrofuran to provide tetrahydrofuran.

2. The process of claim 1 wherein the cis-1,4-dihalobutene-2 is cis-1,4-dichlorobutene-2.

3. The process of claim 1 wherein a phase transfer agent is present in the reaction medium.

4. The process of claim 3 wherein the phase transfer agent is a quaternary ammonium or phosphonium salt.

5. The process of claim 4 wherein the phase transfer agent is tetradecyltrimethylammonium bromide.

6. The process of claim 4 wherein the phase transfer agent is tetradecyltributylphosphonium bromide.

7. The process of claim 3 wherein the phase transfer agent is sodium tetraphenyl boron.

8. The process of claim 1 wherein the water is present in stoichiometric excess.

9. The process of claim 1 wherein the temperature of the reaction medium is from about 20° C. to about 350° C.

10. The process of claim 9 wherein the temperature of the reaction medium is from about 100° C. to about 250° C.

11. The process of claim 1 wherein the pressure of the reaction is from below atmospheric to about 160 atmospheres.

12. The process of claim 11 wherein the pressure of the reaction is from atmospheric to about 50 atmospheres.

13. The process of claim 1 wherein the strong acid is hydriodic acid, sulfuric acid or phosphoric acid.

14. The process of claim 1 wherein from about 0.001 to about 0.1 moles of acid are employed.

15. A process for preparing tetrahydrofuran in a series of steps which comprises:
   (a) reacting butadiene with halogen to provide a mixture of cis-1,4-dihalobutene-2, trans-1,4-dihalobutene-2 and 3,4-dihalobutene-1;
   (b) isomerizing the 3,4-dihalobutene-1 in the presence of an isomerization catalyst to provide a mixture of cis and trans-1,4-dihalobutene-2;
   (c) reacting the mixed cis and trans-1,4-dihalobutene-2 with water in the presence of a catalytically effective amount of strong acid to provide 2,5-dihydrofuran, crotonaldehyde, and by-product hydrohalic acid;
   (d) separating the 2,5-dihydrofuran and crotonaldehyde;

(e) hydrogenating the 2,5-dihydrofuran to provide tetrahydrofuran;

(f) reacting the by-product hydrohalic acid from step (c) with oxygen to provide halogen; and, (g) recycling the halogen to react with a fresh quantity of butadiene in step (a).

16. The process of claim 15 wherein the halogen is chlorine.

17. A process for preparing 2,5-dihydrofuran which comprises reacting a cis-1,4-dihalobutene-2 with water in the presence of a catalytically effective amount of a strong acid.

18. The process of claim 17 wherein the cis-1,4-dihalobutene-2 is 1,4-dichlorobutene-2.

19. The process of claim 17 wherein a phase transfer agent is present in the reaction medium.

20. The process of claim 19 wherein the phase transfer agent is quaternary ammonium or phosphonium salt.

21. The process of claim 20 wherein the phase transfer agent is tetradecyltrimethylammonium bromide.

22. The process of claim 20 wherein the phase transfer agent is tetradecyltributylphosphonium bromide.

23. The process of claim 19 wherein the phase transfer agent is sodium tetraphenyl boron.

24. The process of claim 17 wherein the water is present in stoichiometric excess.

25. The process of claim 17 wherein the temperature of the reaction medium is from about 20° C. to about 350° C.

26. The process of claim 25 wherein the temperature of the reaction medium is from about 100° C. to about 250° C.

27. The process of claim 17 wherein the pressure of the reaction is from below atmospheric to about 160 atmospheres.

28. The process of claim 27 wherein the pressure of the reaction is from atmospheric to about 50 atmospheres.

29. The process of claim 17 wherein the strong acid is hydriodic acid, sulfuric acid or phosphoric acid.

30. The process of claim 17 wherein from about 0.001 to about 0.1 moles of acid are employed.

* * * * *